(12) United States Patent
Timmerbacka et al.

(10) Patent No.: US 6,180,789 B1
(45) Date of Patent: Jan. 30, 2001

(54) METHOD FOR OBTAINING PURE ENANTIOMERS OF A PYRIDAZINONE DERIVATIVE

(75) Inventors: Mika Timmerbacka, Veikkola; Jorma Lehtonen, Kuohu; Veli Pekka Tanninen, Espoo; Esa Muttonen; Jukka Kaukonen, both of Helsinki; Riikka Hyppölä, Espoo; Reijo Bäckström, Helsinki, all of (FI)

(73) Assignee: Orion Corporation, Espoo (FI)

( * ) Notice: Under 35 U.S.C. 154(b), the term of this patent shall be extended for 0 days.

(21) Appl. No.: 09/155,294

(22) PCT Filed: Mar. 27, 1997

(86) PCT No.: PCT/FI97/00196

§ 371 Date: Feb. 4, 1999

§ 102(e) Date: Feb. 4, 1999

(87) PCT Pub. No.: WO97/35841

PCT Pub. Date: Oct. 2, 1997

(30) Foreign Application Priority Data

Mar. 27, 1996 (FI) .................................... 9606474

(51) Int. Cl.[7] ..................... A61K 31/50; C07D 237/14
(52) U.S. Cl. ........................... 544/239; 514/247
(58) Field of Search ............................ 514/247; 544/239

(56) References Cited

U.S. PATENT DOCUMENTS 3,857,889 * 12/1974 Leigh ................................ 260/570.7

FOREIGN PATENT DOCUMENTS

| 208 518 | 9/1991 | (EP) . |
| 565 546 | 3/1995 | (EP) . |
| 383 449 | 9/1995 | (EP) . |
| 92/12135 | 7/1992 | (WO) . |

OTHER PUBLICATIONS

Curran, W.V. et al., "6–Phenyl–4, 5–dihydro–3(2H)–pyridazinones. A Series of Hypotensive Agents", *J. Med. Chem.* 17(3), 1974, 273–281.

Howson, W. et al., "Synthesis and Biological Activity of the Four Stereoisomers of 6–[4–[3–[[2–Hydroxy–3–[4–[2–(cyclopropylmethoxy)ethyl]phenoxy]propyl]amino]propionamido]phenyl]–5–methyl–4,5–dihydro–3(2H)–pyridazinone, a Combined Vasodilator and β–Adrenoceptor Antagonist", *J. Med. Chem.*, 31, 1988, 352–356.

Owings, F.F. et al., "An Enantioselective Synthesis of SK&F 93505, a Key Intermediate for Preparing Cardiotonic Agents", *J. Org. Chem.* 56, 1991, 1963–1966.

* cited by examiner

*Primary Examiner*—Floyd D. Higel
*Assistant Examiner*—Ebenezer Sackey
(74) *Attorney, Agent, or Firm*—Finnegan, Henderson, Farabow, Garrett, & Dunner, L.L.P.

(57) ABSTRACT

The present invention relates to a method for preparing optically active enantiomers of [[4-(1,4,5,6-tetrahydro-4-methyl-6-oxo-3-pyridazinyl)phenyl]-hydrazono] propanedinitrile (I), particularly (−) enantiomer of (I). Furthermore, the invention relates to a novel crystalline polymorphic form of the (−) enantiomer.

16 Claims, 1 Drawing Sheet

METHOD FOR OBTAINING PURE ENANTIOMERS OF A PYRIDAZINONE DERIVATIVE

This is a 371 of PCT/F197/00196 filed on Mar. 27, 1997.

TECHNICAL FIELD

The present invention relates to a method for preparing optically active enantiomers of [[4-(1,4,5,6-tetrahydro-4-methyl-6-oxo-3-pyridazinyl)phenyl]hydrazono]propanedinitrile (I), particularly (−) enantiomer of (I). Furthermore, the invention relates to a novel crystalline polymorphic form of the (−) enantiomer.

BACKGROUND OF THE INVENTION

The racemic mixture of [[4-(1,4,5,6-tetrahydro-4-methyl-6-oxo-3-pyridazinyl)phenyl]hydrazono]propanedinitrile (I) has been described earlier in the applicant's European Patent No. 38:3449 B1. It was shown that compound (I) is potent in the treatment of congestive heart failure and has significant calcium dependent binding to troponin.

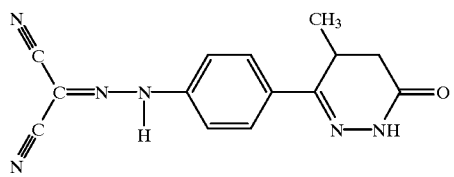

I

Optically active enantiomers of (I) have been earlier described in the applicant's European Patent No. 565546 B1. It was shown that the cardiotonic potency is predominantly due to the (−) enantiomer of (I). A method for preparing pure (−) enantiomer of (I) using optically pure (−) enantiomer of 6-(4-aminophenyl)-4,5-dihydro-5-methyl-3(2H)-pyridazinone (II) as an intermediate compound was also disclosed.

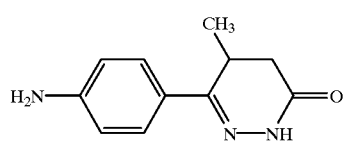

II

The racemic compound (II) can be synthesized by methods known in the literature (J. Med. Chem., 17, 273–281 (1974)). The resolution of the racemic compound (II) has, however, been proved very difficult because the 4-amino group in the molecule is weakly basic. The salts of 6-(4-aminophenyl)-4,5-dihydro-5-methyl-3(2H)-pyridazinone with optically active acids hydrolyse on crystallization readily back to the compound (II) and to the resolving compound which interfere the resolution procedure or make it totally impossible.

The separation of the pure enantiomers of compound (II) on a chiral HPLC-column has been described in European patent application No. 208518. This method is, however, not applicable for industrial scale. An enantioselective seven step synthesis of (−)-6-(4-aminophenyl)-4,5-dihydro-5-methyl-3(2H)-pyridazinone starting from (+)-2-chloropropionic acid has also been described in the literature (J. Org. Chem., 56, 1963 (1991)). The total yield in this method is only 12% giving (−)-6-(4-aminophenyl)-4,5-dihydro-5-methyl-3(2H)-pyridazinone with an optical purity of 97.2%.

In the above mentioned European Patent No. 565546 B1 it was found that the racemic intermediate (II) can be resolved by treating (II) with L- or D-tartaric acid in excess in 2-propanol and recovering the diastereomeric crystalline salt. Optical purity of the product was further increased by dissolving the recovered basified product in dioxane. The racemic residue was crystallized from dioxane and the filtrate was evaporated to dryness yielding the desired pure enantiomer of the intermediate (II). The pure (−) enantiomer of (I) was prepared by treating (−) enantiomer of the intermediate (II) further with sodium nitrite and malononitrile in acidic conditions as described in the above mentioned European Patent No. 383449 B1.

Even if this process gives pure (−) enantiomer of (I), the necessity to use harmful dioxane limits its applicability in the large scale. Therefore there is a need for an improved process for preparing pure (−) enantiomer of (I).

SUMMARY OF THE INVENTION

Figure 1:
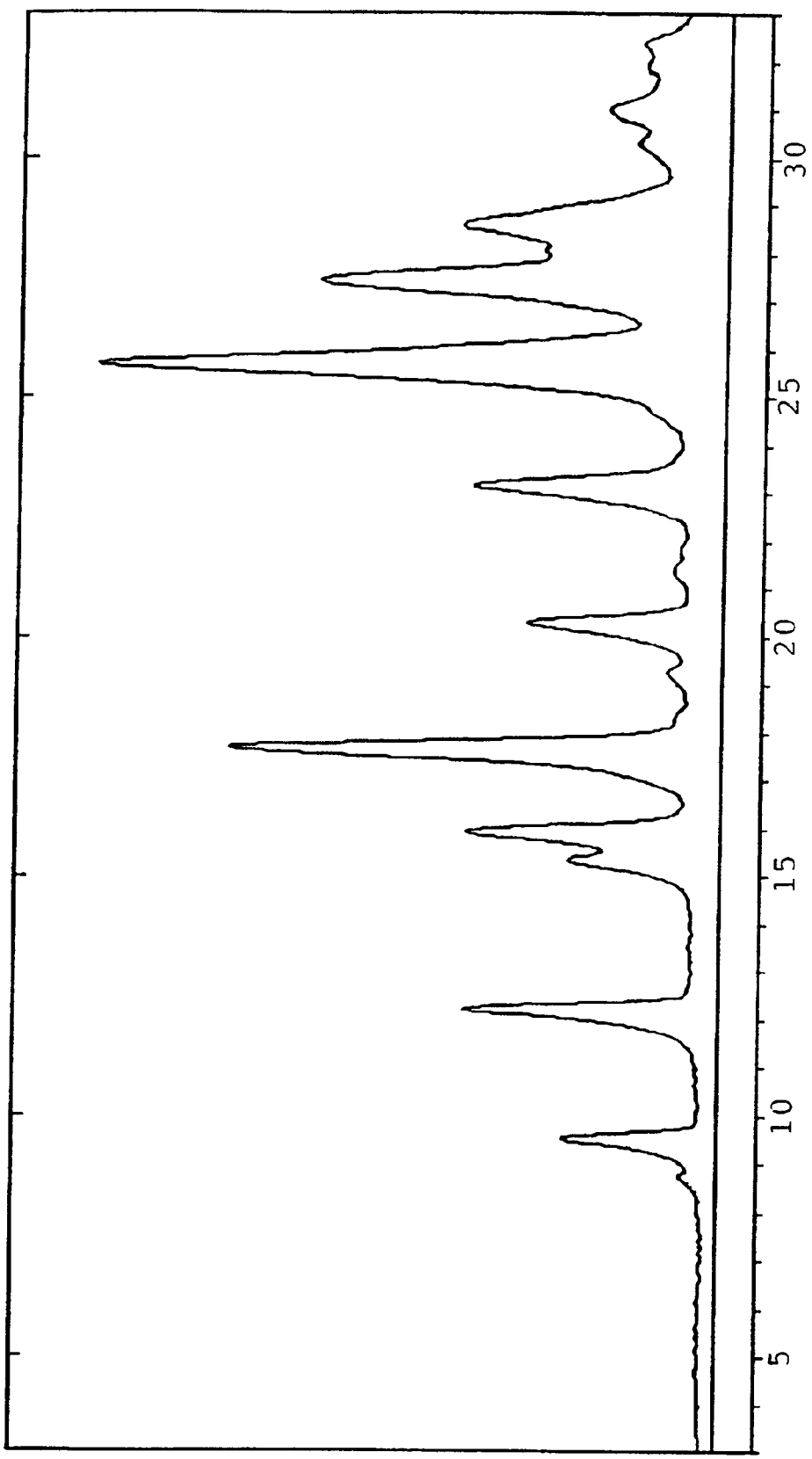
FIG. 1 is the X-ray powder diffraction pattern in 3–33 2θ° range of the polymorphic form I of (−)-[[4-(1,4,5,6-tetrahydro-4-methyl-6-oxo-3-pyridazinyl)-phenyl]hydrazono]propanedinitrile

It has now been found that substantially pure (−) enantiomer of (I) can be prepared more conveniently and without dioxane if the resolution is conducted in two different synthesis stages. The initial resolution step comprises resolving racemic intermediate (II) and the final resolution step comprises resolving the enantiomerically enriched end product (I). It was also found that the initial resolution step results in higher optical purity of intermediate (II) if ethyl acetate is used as solvent instead of 2-propanol. Furthermore it was found that the minor component in a partly enriched enantiomer mixture of end product (I) can be crystallized out from acetone.

Thus the present invention provides a method for preparing optically substantially pure (−)-[[4-(1,4,5,6-tetrahydro-4-methyl-6-oxo-3-pyridazinyl)-phenyl]hydrazono]propanedinitrile the method comprising the steps of
  a) resolving racemic 6-(4-aminophenyl)-4,5-dihydro-5-methyl-3(2H)-pyridazinone by precipitation with a resolving acid in the presence of a solvent,
  b) treating the recovered 6-(4-aminophenyl)-4,5-dihydro-5-methyl-3(2H)-pyridazinone which is enriched in (−) enantiomer with sodium nitrite and malononitrile,
  c) allowing the resulting [[4-(1,4,5,6-tetrahydro-4-methyl-6-oxo-3-pyridazinyl)phenyl]hydrazono]propanedinitrile which is enriched in (−) enantiomer to contact with acetone,
  d) removing the precipitate,
  e) recovering from the mother liquid of step d) the optically substantially pure (−)-[[4-(1,4,5,6-tetrahydro-4-methyl-6-oxo-3-pyridazinyl)phenyl]hydrazono]propanedinitrile by crystallization.

Furthermore the present invention provides a method for preparing optically substantially pure (−)-[[4-(1,4,5,6-tetrahydro-4-methyl-6-oxo-3-pyridazinyl)phenyl]hydrazono]propanedinitrile the method comprising the steps of
  a) suspending [[4-(1,4,5,6-tetrahydro-4-methyl-6-oxo-3-pyridazinyl)-phenyl]hydrazono]propanedinitrile which is enriched in (−) enantiomer in acetone solvent, b) removing the precipitate, c) recovering from the mother liquid of step b) the optically substantially pure (−)-[[4-(1,4,5,6-tetrahydro-4-methyl-6-oxo-3-pyridazinyl)phenyl]hydrazono] propanedinitrile by crystallization.

The present invention also provides a method for the optical resolution of racemic 6-(4-aminophenyl)-4,5-dihydro-5-methyl-3(2H)-pyridazinone which method comprising the steps of a) contacting the racemic mixture with D- or L-tatraric acid in ethyl acetate solvent, b) recovering the crystalline salt; and c) optionally basifying the salt to form the corresponding free base.

Furthermore the present invention provides a novel crystalline polymorphic form I of (−)-[[4-(1,4,5,6-tetrahydro-4-methyl-6-oxo-3-pyridazinyl)-phenyl]hydrazono] propanedinitrile and methods for the preparation thereof.

DETAILED DESCRIPTION

The term "optically substantially pure" means here optical purity over about 90%, preferably over 95%, and more preferably over 99%, expressed as the percent enantiomeric excess. The terms "resolve" and "resolution" are intended to compass the complete or partial separation of the two optical enantiomers.

According to the present invention the racemic compound (II) is preferably resolved by reacting the racemic mixture of (II) with D- or L-tartaric acid in ethyl acetate solvent. Advantageously the ethyl acetate solvent contain from 0 to about 6 w-%, preferably from 2 to 4 w-%, more preferably about 3 w-%, of water. It is preferred to use D- or L-tartaric acid and compound (II) in about equimolar amounts. The diastereomeric salts of (−) 6-(4-aminophenyl)-4,5-dihydro-5-methyl-3(2H)-pyridazinone with D-tartaric acid or corresponding (+) 6-(4-aminophenyl)-4,5-dihydro-5-methyl-3 (2H)-pyridazinone with L-tartaric acid crystallize from ethyl acetate in good yield. The crystalline diastereomeric salt can be filtered and the free base liberated by basifying the salt with e.g. potassium carbonate solution or ammonia. The mother liquid can be recovered after filtering and be further treated in order to recover the enantiomer which was not previously removed by precipitation. The treatment may comprise e.g. cooling the mother liquid and recovering the resulting crystalline diastereomeric salt.

Typically the product obtained by the above described method contains about 90 w-% of the desired enantiomer of (II). The purity of the product can be increased to about 96 w-% by recrystallization. Acetonitrile is the preferred recrystallization solvent. For example, the product which is enriched in (−) enantiomer is recrystallized by adding the product to acetonitrile solvent, refluxing the mixture and filtering precipitate. The filtrate is concentrated, if necessary, and cooled in order to crystallize the (−) enantiomer of (II).

By way of comparison it can be noted that the resolution method of EP 565546 B1 which comprises treating (II) with L- or D-tartaric acid in excess in 2-propanol yields a product containing less than 70 w-% of the desired enantiomer of (II) if the product is not further treated with dioxane.

Partial resolution of compound (II) can be obtained, as shown by the Examples, using other solvent systems than ethyl acetate. Such solvents include isopropanol, isobutanol, isopropyl acetate, butyl acetate, acetone and acetonitrile. Also the use of other resolving acids than D- or L-tartaric acid can result in partial resolution of compound (II), e.g.

benzoic acid or sulphuric acid. However, the method of using D- or L-tartaric acid in ethyl acetate or aqueous ethyl acetate solvent provides the highest optical purities for compound (II) according to the invention.

The end product (−)-[[4-(1,4,5,6-tetrahydro-4-methyl-6-oxo-3-pyridazinyl)phenyl]hydrazono]propanedinitrile (I) is prepared from 6-(4-aminophenyl)-4,5-dihydro-5-methyl-3 (2H)-pyridazinone intermediate (II) which is enriched in (−) enantiomer by allowing the intermediate to react with sodium nitrite and malononitrile in acidic conditions as described in EP 383449 B1. Compound (I) which is enriched in (−) enantiomer is then recovered.

It has been found that the minor component in a partly enriched enantiomer mixture of compound (I) can be filtered out from acetone leaving the rest of the major component in solution. This allows recovering the substantially pure (−) enantiomer of (I) from the mother solution by crystallization.

Thus, in order to prepare substantially pure (−) enantiomer of (I) the previously recovered compound (I) which is enriched in (−) enantiomer is suspended in acetone solvent, which preferably contains up to 2 w-% of water. The mixture is refluxed and the precipitate is filtered. The filtrate is then concentrated, if necessary, and cooled to about 0–(−5)° C. The precipitated crystalline (−) enantiomer of (I) is recovered. The product contains typically more than 99 w-% of the desired (−) enantiomer of (I) and is therefore suitable for use as a medicament.

The enantiomeric purities of the products were determined by the high performance liquid chromatography (HPLC,). The enantiomers of compound (II) were separated by using a cellulose-type chiral column (Chiralcel OJ 25×0.46 cm). The mobile phase consisted of ethanol. The flow rate was 0.5 ml/min. The enantiomers of compound (I) were separated by using a β-cyclodextrin column (Cyclobond I Beta, 4.6×250 mm). The mobile phase consisted of 36% methanol in water buffered to pH 6.0 with 1% triethylammonium acetate. The flow rate was 0.8 ml/min.

It was furthermore discovered that the above described methods of preparing substantially pure (−) enantiomer of (I) yield a novel crystallographically pure polymorphic form of (−)-[[4-(1,4,5,6-tetrahydro-4-methyl-6-oxo-3-pyridazinyl)phenyl]hydrazono]propanedinitrile, herein designated, for convenience, as polymorphic form I. The important advantage of the polymorphic form I is its high dissolution rate in water. This makes the polymorphic form I especially useful in pharmaceutical preparations of (−)-[[4-(1,4,5,6-tetrahydro-4-methyl-6-oxo-3-pyridazinyl) phenyl]hydrazono]propanedinitrile.

It was also found that the crystallographical purity of the polymorphic form I can be, if necessary, improved by heating the obtained (−) enantiomer product at a temperature of at least about 70° C. for a time period necessary for the formation of crystallographically pure polymorphic form I. The suitable temperature is typically within the range of 70–160° C., preferably 80–130° C. The time period is typically within the range of 1–48 h, preferably 4–24 h. This treatment may be part of the drying process of the product and may be carried out in vacuum.

The polymorphic form I of (−)-[[4-(1,4,5,6-tetrahydro-4-methyl-6-oxo-3-pyridazinyl)phenyl]hydrazono] propanedinitrile is characterized by the X-ray crystallography. The X-ray powder diffraction pattern of the polymorphic form I in 3–33 2θ° range is in FIG. 1 and the crystallographic data in Table 1.

The diffraction pattern was measured by the X-ray powder diffraction (XRPD) equipment, Siemens D 500 (Siemens AG, Karlsruhe, Germany). A copper target X-ray (wavelength 0.1541 nm) tube was operated with the power of 40 kV×40 mA. For X-ray powder diffraction analysis the samples were mounted by loosely pressing about 500 mg of the powder to the specific cylindrical sample stage which has a diameter of 20 mm and height of approximately 2 mm. Mathematical evaluation of diffraction patterns was performed with aid of Diffrac AT V3.1 software package. Main characteristics of the diffraction patterns as 2θ-values and relative peak intensities were produced as out-put data.

TABLE 1

X-ray diffraction angles (2θ°) and corresponding relative intensity values (only %-values ≧5%) of polymorphic form I.

| 2θ angle(°) | Relative intensity (%) |
|---|---|
| 8.7 | 5 |
| 9.5 | 23 |
| 12.2 | 34 |
| 15.4 | 25 |
| 15.9 | 40 |
| 17.7 | 72 |
| 18.4 | 8 |
| 19.2 | 9 |
| 20.3 | 27 |
| 21.4 | 8 |
| 21.8 | 8 |
| 23.1 | 36 |
| 24.6 | 12 |
| 25.7 | 100 |
| 27.4 | 64 |

The relative intensity values may vary remarkably because of different orientation of crystals. Therefore, the relative intensity values given in Table 1 can be regarded as representative only for, e.g. non-micronized powder.

The following examples are meant to further illustrate the invention.

EXAMPLE 1

(−)-6-(4-aminophenyl)-4,5-dihydro-5-methyl-3(2H)-pyridazinone 100 g of racemic 6-(4-aminophenyl)-4,5-dihydro-5-methyl-3(2H)-pyridazinone was added to 2997 ml of ethyl acetate, 94,4 ml of water, 77,8 g of D-tartaric acid and 1.0 g of D-tartaric salt of (−)-6-(4-aminophenyl)-4,5-dihydro-5-methyl-3(2H)-pyridazinone under nitrogen. The mixture was stirred in room temperature for 1.5 h. Thereafter the mixture was heated to 65° C. and stirred for 2 h. The precipitate was filtered hot and washed with 561 ml of ethyl acetate. The precipitate was mixed with 400 ml of water and pH of the mixture was adjusted to 9–10 with $NH_3$. The mixture was cooled to 0° C. and stirred for 2 h. The precipitate was filtered, washed three times with 322 ml of cold water and dried in vacuum in 50° C. Yield was 35 g and the ratio of (−/+) enantiomers 93/7%. The product (35 g) was further added to 777 ml of acetonitrile and 2.0 g of celite under nitrogen. The precipitate was filtered hot and washed with 33 ml of acetonitrile which was added to the filtrate. 253 ml of acetonitrile was distilled from the filtrate and the remaining mixture was cooled to −5° C. The precipitate was filtered, washed with 76 ml of acetonitrile and dried in vacuum in 50° C. Yield 24.5 g. Ratio of (−/+) enantiomers 96/4%.

EXAMPLE 2

(−)-6-(4-aminophenyl)-4,5-dihydro-5-methyl-3(2H)-pyridazinone 50 g of racemic 6-(4-aminophenyl)-4,5-dihydro-5-methyl-3(2H)-pyridazinone was added to 1500 ml of ethyl acetate, 46 ml of water, 37.5 g of D-tartaric acid and 1.0 g of D-tartaric salt of (−)-6-(4-aminophenyl)-4,5-dihydro-5-methyl-3(2H)-pyridazinone. The mixture was stirred in room temperature for 1.5 h. Thereafter the mixture was heated to 65±3° C. and stirred for 3 h. The precipitate was filtered hot and washed with 116 ml of ethyl acetate of room temperature. The precipitate was mixed with 200 ml of water of room temperature and 44 g of potassium bicarbonate in 90 ml of water was slowly added. It was checked that pH was over 9.0. The mixture was cooled to 0±3° C. and stirred for 2 h. The precipitate was filtered, washed three times with 120 ml of cold water and dried in vacuum in 50±5° C. Yield 17.87 g. Ratio of (−/+) enantiomers 90.7/8.6%.

EXAMPLE 3

(−)-6-(4-aminophenyl)-4,5-dihydro-5-methyl-3(2H)-pyridazinone 50 g of racemic 6-(4-aminophenyl)-4,5-dihydro-5-methyl-3(2H)-pyridazinone was added to 1500 ml of ethyl acetate, 45 ml of water and 37.3 g of L-tartaric acid. The mixture was heated to 60° C. and stirred for 2 h. The precipitate was filtered and the filtrate was cooled to −10° C. and kept in this temperature for 2 h. The precipitate that crystallized from the filtrate was filtered and dried in vacuum in 50° C. The precipitate was mixed with 200 ml of water in room temperature and 43 g of potassium bicarbonate in 90 ml of water was slowly added. It was checked that pH was over 9.0. The mixture was cooled to 0° C. and stirred for 2 h. The precipitate was filtered, washed three times with 120 ml of cold water and dried in vacuum in 50±5° C. Yield 20.61 g. Ratio of (−/+) enantiomers 78.7/21.2%.

EXAMPLE 4

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 30 ml of isopropanol and 0.6 g of benzoic acid. The mixture was boiled until dissolved and cooled to room temperature whereupon the product crystallized. The crystalline product was filtered and the ratio of the benzoic acid salts of the enantiomers was determined. Ratio of (−/+) enantiomers 74.1/25.5%.

EXAMPLE 5

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 30 ml of isopropanol and 0.48 g of concentrated sulphuric acid. The mixture was boiled and cooled to room temperature. The crystalline product was filtered and the ratio of the sulphate salts of the enantiomers was determined. Ratio of (−/+) enantiomers 65.1/34.9%

EXAMPLE 6

(−)-6-(4-aminophenyl)-4,5-dihydro-5-methyl-3(2H)-pyridazinone 5 g of racemic 6-(4-aminophenyl)-4,5-dihydro-5-methyl-3(2H)-pyridazinone was added to 75 ml of ethyl acetate, 3.1 ml of water and 3.73 g of L-tartaric acid. The mixture was boiled for 3.5 h, the precipitate was filtered and the filtrate was cooled to −10° C. The precipitate that crystallized from the filtrate was filtered and dried in vacuum in 50° C. Yield 2.86 g. The ratio of the L-tartrate salts of the enantiomers (−/+) 72/27%.

EXAMPLE 7

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 20 ml of isobutanol and 0.75 g of L-tartaric acid. The mixture was boiled and cooled. A sample was taken as soon as the crystallization started (at 64° C). The ratio of the L-tartrate salts of the enantiomers (−/+) 53/46%. 0.6 ml of water was added to the mixture, the mixture was boiled, cooled and a sample was taken at the beginning of the crystallization (at 64° C.). The ratio of the L-tartrate salts of the enantiomers (−/+) 60/40%. Again 0.6 ml of water was added to the mixture and the previous procedure was repeated. The product started crystallize at 46° C. The ratio of the L-tartrate salts of the enantiomers (−/+) 56/44%.

EXAMPLE 8

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 60 ml of isopropyl acetate and 0.75 g of L-tartaric acid. The mixture was boiled and a sample was taken from the undissolved precipitate. The ratio of the L-tartrate salts of the enantiomers (−/+) 44/56%. 1.2 ml of water was added to the mixture, whereupon the precipitate dissolved. The mixture was cooled and a sample was taken at the beginning of the crystallization (at 68° C.). The ratio of the L-tartrate salts of the enantiomers (−/+) 24/76%.

EXAMPLE 9

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 50 ml of ethyl acetate, 0.75 g of L-tartaric acid and A) 0.5, B) 1.0 or C) 1.5 ml of water. The mixture was boiled and cooled. The mixture was filtered and a sample was taken from the precipitate and from the filtrate at the beginning of the crystallization. The ratio of the L-tartrate salts of the enantiomers (−/+) %:

|    | Precipitate | Filtrate | Crystallization temperature, ° C. |
|----|-------------|----------|-----------------------------------|
| A) | 29/71       | 66/30    | 52                                |
| B) | 22/77       | 65/32    | 54                                |
| C) | 20/80       | 85/13    | 50                                |

EXAMPLE 10

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 50 ml of butyl acetate and 0.75 g of L-tartaric acid. The mixture was boiled and cooled. The mixture was filtered and a sample was taken from the precipitate at the beginning of the crystallization (64° C.). The ratio of the L-tartrate salts of the enetntiomers (−/+) 44/55%.

EXAMPLE 11

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 10 ml of acetone and 0.75 g of L-tartaric acid. The mixture was warmed until dissolved (54° C.) and cooled to 0° C. A sample was taken from the precipitate. The ratio of the L-tartrate salts of the enantiomers (−/+) 49/42%.

EXAMPLE 12

(−)-6-(4-aminophenyl)-4,5-dihydro-5-methyl-3(2H)-pyridazinone 1 g of racemic 6-(4-aminophenyl)-4,5-dihydro-5-methyl-3(2H)-pyridazinone was added to 44 ml of acetonitrile and 0.75 g of L-tartaric acid. The mixture was boiled and cooled. A sample was taken from the precipitate at the beginning of the crystallization. The ratio of the L-tartrate salts of the enantiomers (−/+) 43/50%.

EXAMPLE 13

(−)-[[4-(1,4,5,6-tetrahydro-4-methyl-6-oxo-3-pyridazinyl)phenyl]hydrazono]propanedinitrile The 6-(4-aminophenyl)-4,5-dihydro-5-methyl-3(2H)-pyridazinone obtained in Example 2 with (−/+) resolution % of 96/4 was treated with sodium nitrite and malononitrile as described in the European Patent No. 383449 B1. 10 g of the recovered [[4-(1,4,5,6-tetrahydro-4-methyl-6-oxo-3-pyridazinyl)phenyl]hydrazono]propanedinitrile with (−/+) resolution % of 96/4 was added to 150 ml of acetone, 0.9 ml of water, 0.2 g of activated carbon and 0.4 g of Celite. The mixture was refluxed for 1 h and filtered hot. The precipitate was washed with 10 ml of hot acetone which was added the to the filtrate. The filtrate was refluxed for 30 min. 61 ml of acetone was distilled from the filtrate and the remaining mixture was cooled to 0–(−5) ° C. The mixture was filtered and washed with 10 ml of cold acetone. The crystalline product was dried in vacuum in 50° C. The product contained over 99% of the desired (−) enantiomer and the yield was 6.8 mg. The product was substantially pure crystalline polymorphic form I.

EXAMPLE 14

(−)-[[4-(1,4,5,6-tetrahydro-4-methyl-6-oxo-3-pyridazinyl)phenyl]hydrazono]propanedinitrile The title product was prepared as in Example 13 except that the drying was carried out in 100° C. for 5 h. The product was pure crystalline polymorphic form I.

EXAMPLE 15

(−)-[[4-(1,4,5,6-tetrahydro-4-methy-6-oxo-3-pyridazinyl)phenyl]hydrazono]propanedinitrile The title product was prepared as in Example 13 except that the drying was carried out in 120° C. for 18 h. The product was pure crystalline polymorphic form I.

What is claimed is:

1. A method for preparing optically substantially pure (−)-[[4-(1,4,5,6-tetrahydro-4-methyl-6-oxo-3-pyridazinyl)phenyl]hydrazono]propanedinitrile comprising the steps of a) resolving racemic 6-(4-aminophenyl)-4,5-dihydro-5-methyl-3(2H)-pyridazinone by precipitation with a resolving acid in the presence of a solvent, b) treating the recovered 6-(4-aminophenyl)-4,5-dihydro-5-methyl-3(2H)-pyridazinone which is enriched in (−) enantiomer with sodium nitrite and malononitrile, c) allowing the resulting [[4-(1,4,5,6-tetrahydro-4-methyl-6-oxo-3-pyridazinyl)phenyl]hydrazono]propanedinitrile which is enriched in (−) enantiomer to mix with acetone, d) removing the precipitate, e) recovering from the mother liquid of step d) the optically substantially pure (−)-[[4-(1,4,5,6-tetrahydro-4-methyl-6-oxo-3-pyridazinyl)phenyl]hydrazono]propanedinitrile by crystallization.

2. The method according to claim 1 wherein the solvent is ethyl acetate, isopropanol, isobutanol, isopropyl acetate, butyl acetate, acetone or acetonitrile.

3. The method according to claim 2 wherein the solvent is ethyl acetate.

4. The method according to claim 3 wherein the solvent comprises up to 6 w-% of water.

5. The method according to claim 1, wherein the resolving acid is D- or L-tartaric acid.

6. A method for preparing optically substantially pure (−)-[[4-(1,4,5,6-tetrahydro-4-methyl-6-oxo-3-pyridazinyl)phenyl]hydrazono]propanedinitrile comprising the steps of a) suspending [[4-(1,4,5,6-tetrahydro-4-methyl-6-oxo-3-pyridazinyl)-phenyl]hydrazono]propanedinitrile which is enriched in (−) enantiomer in acetone solvent, b) removing the precipitate, c) recovering from the mother liquid of step b) the optically substantially pure (−)-[[4-(1,4,5,6-tetrahydro-4-methyl-6-oxo-3-pyridazinyl)phenyl]hydrazono]propanedinitrile by crystallization.

7. The method according to claim 6 wherein the acetone solvent comprises up to 2 w-% of water.

8. The method for the optical resolution of racemic 6-(4-aminophenyl)-4,5-dihydro-5-methyl-3(2H)-pyridazinone which method comprising the steps of a) reacting the racemic mixture with D- or L-tatraric acid in ethyl acetate solvent, b) recovering the crystalline salt; and c) optionally basifying the salt to form the corresponding free base.

9. The method according to claim 8, wherein the solvent comprises up to 6 w-% of water.

10. Crystalline polymorphic form I of (−)-[[4-(1,4,5,6-tetrahydro-4-methyl-6-oxo-3-pyridazinyl)phenyl]hydrazono]propanedinitrile wherein the X-ray diffraction pattern has the following peak positions:

| 2θ angle(°) |
| --- |
| 8.7 |
| 9.5 |
| 12.2 |
| 15.4 |
| 15.9 |
| 17.7 |
| 18.4 |
| 19.2 |
| 20.3 |
| 21.4 |
| 21.8 |
| 23.1 |
| 24.6 |
| 25.7 |
| 27.4. |

11. A method for obtaining crystalline polymorphic form I of claim 10 which comprises heating optically substantially pure (−)-[[4-(1,4,5,6-tetrahydro-4-methyl-6-oxo-3-pyridazinyl)phenyl]hydrazono]propanedinitrile which is a mixture of the polymorphic form I and any other polymorphic form at a temperature of at least 70° C. for a time period necessary for the formation of pure polymorphic form I.

12. The method according to claim 4, wherein the solvent comprises 2–4 w-% of water.

13. The method according to claim 12, wherein the solvent comprises about 3 w-% of water.

14. The method according to claim 9, wherein the solvent comprises 2–4 w-% of water.

15. The method according to claim 14, wherein the solvent comprises about 3 w-% of water.

16. A method for obtaining crystalline polymorphic form I of (−)-[[4-(1,4,5,6-tetrahydro-4-methyl-6-oxo-3-pyridazinyl)phenyl]hydrazono]propanedinitrile wherein the X-ray diffraction pattern has the following peak positions:

| 2θ angle(°) |
| --- |
| 8.7 |
| 9.5 |
| 12.2 |
| 15.4 |
| 15.9 |
| 17.7 |
| 18.4 |
| 19.2 |
| 20.3 |
| 21.4 |
| 21.8 |
| 23.1 |
| 24.6 |
| 25.7 |
| 27.4 | which comprises preparing optically substantially pure (−)-[[4-(1,4,5,6-tetrahydro-4-methyl-6-oxo-3-pyridazinyl)phenyl]hydrazono]propanedinitrile according to any of claims 1–7 or 13–14.

* * * * *

UNITED STATES PATENT AND TRADEMARK OFFICE
CERTIFICATE OF CORRECTION

PATENT NO. : 6,180,789 B1
DATED : January 30, 2001
INVENTOR(S) : Mika Timmerbacka et al.

It is certified that error appears in the above-identified patent and that said Letters Patent is hereby corrected as shown below:

Title Page,
Delete the text of the Abstract and replace with the following:

"A method for preparing optically substantially pure (-)-[[4-(1,4,5,6-tetrahydro-4-methyl-6-oxo-3-pyridazinyl)phenyl]hydrazono] propanedinitrile from racemic 6-(4-aminophenyl)-4,5-dihydro-5-methyl-3(2H)-pyridazinone intermediate is described. The end product is is useful as a cardiotonic agent. A novel crystalline polymorphic form of the end product is also described."

Column 9,
Line 51, "L-tatraric" should read -- L-tartaric --.

Column 10,
Line 60, "claims 1-7 or 13-14" should read -- claims 1-7or 12-13 --.

Signed and Sealed this

Twenty-first Day of August, 2001

Attest:

*Nicholas P. Godici*

NICHOLAS P. GODICI
*Attesting Officer*   *Acting Director of the United States Patent and Trademark Office*